United States Patent
Last et al.

(10) Patent No.: US 9,663,474 B2
(45) Date of Patent: May 30, 2017

(54) HETEROCYCLIC SUBSTITUTED 2-AMINO QUINAZOLINE DERIVATIVES FOR THE TREATMENT OF VIRAL INFECTIONS

(71) Applicant: Janssen Sciences Ireland UC, Little Island (IE)

(72) Inventors: Stefaan Julien Last, Lint (BE); David Craig McGowan, Brussels (BE); Werner Embrechts, Beerse (BE); Serge Maria Aloysius Pieters, AR Hulst (NL); Tim Hugo Maria Jonckers, Heist-op-den-Berg (BE); Pierre Jean-Marie Bernard Raboisson, Rosieres (BE)

(73) Assignee: JANSSEN SCIENCES IRELAND UC, Little Island, County Cork (IE)

( * ) Notice: Subject to any disclaimer, the term of this patent is extended or adjusted under 35 U.S.C. 154(b) by 0 days.

(21) Appl. No.: 14/443,305

(22) PCT Filed: Nov. 15, 2013

(86) PCT No.: PCT/EP2013/073901
§ 371 (c)(1),
(2) Date: May 15, 2015

(87) PCT Pub. No.: WO2014/076221
PCT Pub. Date: May 22, 2014

(65) Prior Publication Data
US 2015/0284339 A1 Oct. 8, 2015

(30) Foreign Application Priority Data
Nov. 16, 2012 (EP) .................................... 12192970

(51) Int. Cl.
C07D 239/84 (2006.01)
C07D 239/95 (2006.01)
C07D 401/12 (2006.01)
C07D 403/12 (2006.01)
C07D 413/12 (2006.01)
C07D 417/12 (2006.01)

(52) U.S. Cl.
CPC ......... C07D 239/84 (2013.01); C07D 239/95 (2013.01); C07D 401/12 (2013.01); C07D 403/12 (2013.01); C07D 413/12 (2013.01); C07D 417/12 (2013.01)

(58) Field of Classification Search
CPC .................................................. C07D 401/07
See application file for complete search history.

(56) References Cited

FOREIGN PATENT DOCUMENTS

| JP | 2000053653 | * | 2/1998 | ........... C07D 407/11 |
|---|---|---|---|---|
| JP | 2000-53653 | A | 2/2000 | |
| WO | WO 98/01448 | A1 | 1/1998 | |
| WO | WO 99/28321 | A1 | 6/1999 | |
| WO | WO 2006/117670 | A1 | 11/2006 | |
| WO | WO 2008/009078 | A2 | 1/2008 | |
| WO | WO 2009/067081 | A1 | 5/2009 | |
| WO | WO 2012/156498 | A1 | 11/2012 | |

OTHER PUBLICATIONS

Yin et al., J'nal of Org. Chem. (2012), 77(6), 2649-2658.*
Vippagunta et al. (2001).*
Hoffmann, J.A., "The immune response of Drosophila", Nature, 426, p. 33-38, 2003.
Takeda, K. et al., "Toll-Like Receptors", Annual Rev. Immunology, 21, p. 335-376, 2003.
Ulevitch, R. J., "Therapeutics Targeting the Innate Immune System", Nature Reviews: Immunology, 4, p. 512-520, 2004.
Horscroft, Nigel J. et al., "Antiviral applications of Toll-like receptor agonists", J. Antimicrob. Chemother., Jan. 18, 2016, pp. 1-13.
Thomas, Amy et al., "Investigating Toll-Like Receptor Agonists for Potential to Treat Hepatitis C Virus Infection", Antimicrobial Agents and Chemotherapy, Aug. 2007, vol. 51, No. 8, pp. 2969-2978.
Makkouk, Amani et al., "The potential use of toll-like receptor (TLR) agonists and antagonists as prophylactic and/or therapeutic agents", Immunopharmacology and Immunotoxicology, 2009; 31(3): 331-338.
O'Hara et al"Regioselective Synthesis of Imidazo[4,5g]Quinazoline Quinone Nucleosides and Quinazoline Amino Nudeosides. Studies of Their Xanthine Oxidase and Purine Nucleoside Phosphorylase Substrate Activity" J. Org Chem1991 vol. 56 pp. 776-785.
International Search Report and Written Opinion for Corresponding PCT/EP2013/073901 Mailed December 16, 2013.
Extended European Searchc Report for European Application EP12192970.7 Mailed January 1, 2013.

* cited by examiner

Primary Examiner — Paul V Ward

(57) ABSTRACT

This invention relates to heterocyclic substituted 2-amino-quinazoline derivatives, processes for their preparation, pharmaceutical compositions, and their use in treating viral infections.

9 Claims, No Drawings

HETEROCYCLIC SUBSTITUTED 2-AMINO QUINAZOLINE DERIVATIVES FOR THE TREATMENT OF VIRAL INFECTIONS

This application is a 35 U.S.C. §371 nationalization of PCT application PCT/EP2013/073901 filed Nov. 15, 2013, which claims priority to European patent application EP 12192970.7 filed Nov. 16, 2012, both of which are incorporated herein by reference.

Sequence Listing

The instant application contains a Sequence Listing which has been submitted electronically in ASCII format and is hereby incorporated by reference in its entirety. Said ASCII copy, created on Apr. 4, 2017, is named TIP0289USPCT_SL.txt and is 587 bytes in size.

This invention relates to heterocyclic substituted 2-amino-quinazoline derivatives, processes for their preparation, pharmaceutical compositions, and their use in treating viral infections.

The present invention relates to the use of heterocyclic substituted 2-amino-quinazoline derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For reviews on TLRs see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, and an improved safety profile compared to the compounds of the prior art.

In accordance with the present invention a compound of formula (I) is provided

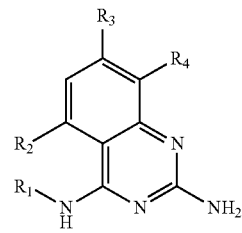

or a pharmaceutically acceptable salt, tautomer(s), stereo-isomeric forms, solvate or polymorph thereof, wherein
R$_1$ is any of the following structures

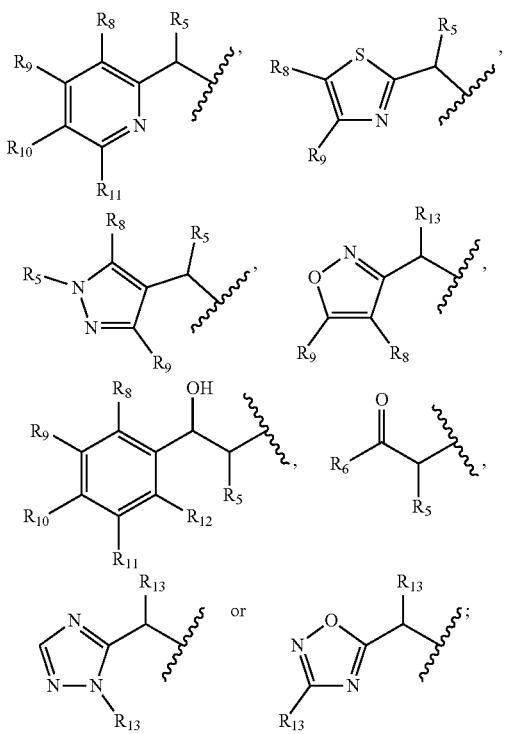

R$_2$ is hydrogen, —O—(C$_{1-3}$)-alkyl, halogen, (C$_{1-3}$)-alkyl, —O—(C$_{1-3}$)-alkyl-O—(C$_{1-3}$)— alkyl or CH$_2$OH;

R$_3$ is hydrogen, —O—(C$_{1-3}$)-alkyl, halogen, (C$_{1-3}$)-alkyl or –C(=O)—R$_7$ wherein R$_7$ is —O—(C$_{1-3}$)-alkyl, NH$_2$, NH(CH$_3$), N(CH$_3$)$_2$, N(CH$_3$)(C$_{1-3}$)-alkyl, N((C$_{1-3}$)-alkyl)$_2$ or pyrolidine;

R$_4$ is hydrogen or fluorine;

R$_5$ is (C$_{1-3}$)-alkyl, (C$_{1-3}$)-fluoro-alkyl or CH$_2$OH;

R$_6$ is NH$_2$, NH(CH$_3$) or N(CH$_3$)$_2$, (hetero)-anilines optionally substituted with one or more R$_8$, R$_9$, R$_{10}$ R$_{11}$ or R$_{12}$ or (hetero)-benzylamines optionally substituted with one or more R$_8$, R$_9$, R$_{10}$ R$_{11}$ or R$_{12}$, R$_8$, R$_9$, R$_{10}$, R$_{11}$ and R$_{12}$ which are the same or different, are each independently selected from hydrogen, (C$_{1-3}$)-alkyl, —O—(C$_{1-3}$)-alkyl or halogen and R$_{13}$ is hydrogen, (C$_{1-3}$)-alkyl or (C$_{1-3}$)-fluoro-alkyl.

Preferred compounds according to the invention are compounds with the numbers 12 and 29 as depicted in Table II.

The compounds of formula (I) and their pharmaceutically acceptable salts, tautomer(s), stereo-isomeric forms, solvate or polymorph thereof have activity as pharmaceuticals, in particular as modulators of Toll-Like Receptors (especially TLR7 and/or TLR8 activity).

In a further aspect the present invention provides a pharmaceutical composition comprising a compound of formula (I) or a pharmaceutically acceptable salt, tautomer, stereo-isomeric form, solvate or polymorph thereof together with one or more pharmaceutically acceptable excipients, diluents or carriers.

Furthermore a compound of formula (I) or a pharmaceutically acceptable salt, solvate, tautomer, stereo-isomeric form or polymorph thereof according to the current invention, or a pharmaceutical composition comprising said compound of formula (I) or a pharmaceutically acceptable salt, solvate, tautomer, stereo-isomeric form or polymorph thereof can be used as a medicament.

Another aspect of the invention is that a compound of formula (I) or its pharmaceutically acceptable salt, solvate, tautomer, stereo-isomeric form or polymorph thereof, or said pharmaceutical composition comprising said compound of formula (I) or a pharmaceutically acceptable salt, solvate, tautomer, stereo-isomeric form or polymorph thereof can be used accordingly in the treatment of a disorder in which the modulation of TLR7 and/or TLR8 is involved.

The term "$(C_{1-3})$-alkyl" refers to a straight-chain, branched-chain or cyclic saturated aliphatic hydrocarbon containing the specified number of carbon atoms.

The term "$(C_{1-3})$-fluoro-alkyl" refers to a straight-chain, branched-chain or cyclic saturated aliphatic hydrocarbon containing the specified number of carbon atoms where one or more hydrogen atoms was replaced by a fluorine atom.

The term "halogen" refers to fluorine, chlorine, bromine or iodine, preferably to fluorine and chlorine.

The term "aniline" refers a compound with the formula $C_6H_5NR_{13}$— consisting of a phenyl group attached to an amino group; with "(hetero)-aniline" is meant that in the aromatic ring 1-3 nitrogen atoms, preferably 1 nitrogen atom, are present.

The term "benzylamine" means a compound of the formula $C_6H_5CH_2NR_{13}$— consisting of a benzyl group, $C_6H_5CH_2$, attached to an amine functional group; with "(hetero)-benzylamine" is meant that in the aromatic ring 1-3 nitrogen atoms, preferably 1 nitrogen atom, are present.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. If a compound contains an at least disubstituted non-aromatic cyclic group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Preparation of Compounds of Formula (I)

Compounds of formula (I) are prepared according to scheme 1. Substituted anthranilic esters or acids (II) were heated under acidic conditions in the presence of excess cyanamide, using an alcoholic solvent (e.g. ethanol) or diglyme according to the method described in the literature (O'Hara et. al. JOC (1991) 56, p 776). Subsequent amine substitution of the 2-amino-4-hydroxyquinazolines (III) can proceed via a coupling agent such as BOP or PyBOP in the presence of DBU and the amine in a polar aprotic solvent (e.g. DMF).

Scheme 1:

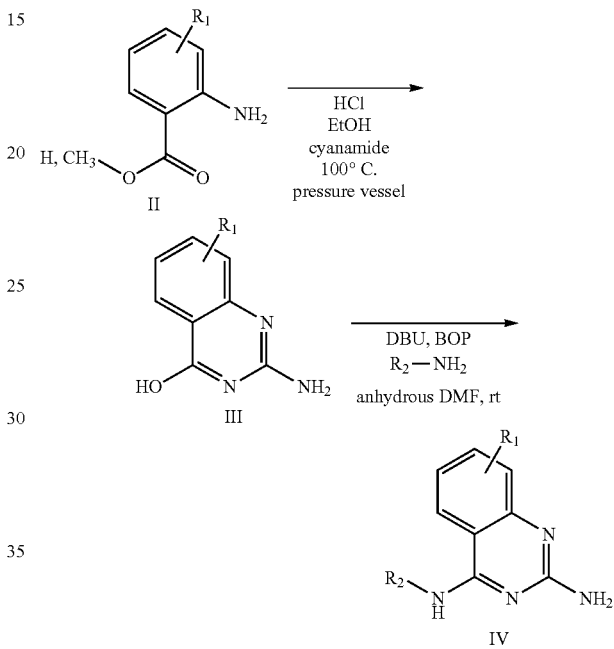

EXPERIMENTAL SECTION

General procedure of making a substituted 2-amino-4-hydroxyquinazoline

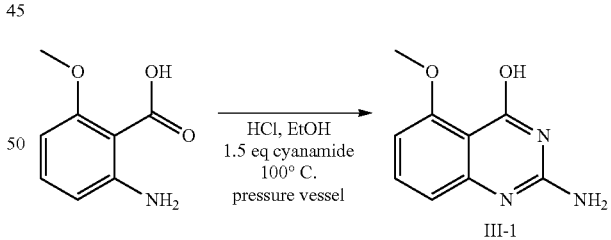

Into a 500 mL pressure vessel equipped with a magnetic stir bar was placed 2-amino-6-methoxybenzoic acid (25 g, 149.6 mmol), ethanol (200 mL), cyanamide (9.43 g, 224 mmol), and concentrated HCl (6 mL). The mixture was allowed to stir at 100° C. for 16 h. The reaction mixture was allowed to cool to room temperature and the solids were isolated via filtration and washed with ethanol and DIPE. The crude product was dried under vacuum at 50° C. to obtain an off white solid.

LC-MS m/z=192 (M+H)

$^1$H NMR (400 MHz, DMSO-$d_6$) δ ppm 3.88 (s, 3H), 6.96 (dd, J=8.2, 3.1 Hz, 2H), 7.69 (t, J=8.3 Hz, 1H), 8.28 (br. s., 2H), 12.67 (br. s., 1H)

TABLE I

Compounds of formula (III).
The following intermediates were prepared according to the method to prepare III-1.

| # | STRUCTURE | H NMR | LCMS (M + H)+ |
|---|---|---|---|
| 1 | 5-fluoro-2-amino-quinazolin-4-ol | $^1$H NMR (400 MHz, DMSO-d$_6$) δ ppm 6.98 (dd, J = 11.0, 8.3 Hz, 1 H), 7.13 (d, J = 8.3 Hz, 1 H), 7.51 (br. s., 2 H), 7.64 (td, J = 8.3, 5.8 Hz, 1 H), 12.30 (br. s, 1 H) | 180 |
| 2 | 7-fluoro-2-amino-quinazolin-4-ol | $^1$H NMR (400 MHz, DMSO-d$_6$) δ ppm 7.01-7.16 (m, 2 H), 7.56 (br. s., 2 H), 7.99 (t, J = 7.7 Hz, 1 H), 10.38-13.48 (m, 1 H) | 180 |
| 3 | 8-fluoro-2-amino-quinazolin-4-ol | $^1$H NMR (400 MHz, DMSO-d$_6$) δ ppm 6.51-6.67 (m, 2H), 7.00-7.08 (m, 1H), 7.42 (ddd, J = 11.2, 7.9 1.3 Hz, 1H), 7.69 (dd, J = 7.9, 0.6 Hz, 1H), 11.08 (br. s., 1H) | 180 |
| 4 | 7-methyl-2-amino-quinazolin-4-ol | $^1$H NMR (400 MHz, DMSO-d$_6$) δ ppm 2.43 (s, 3 H), 7.22 (d, J = 1.0 Hz, 1 H), 7.24 (s, 1 H), 7.89 (d, J = 8.0 Hz, 1 H), 8.29 (br. s., 2 H), 12.65 (br. s, 1 H) | 176 |
| 5 | 7-methoxy-2-amino-quinazolin-4-ol | Not available | 192 |
| 6 | 7-chloro-2-amino-quinazolin-4-ol | $^1$H NMR (400 MHz, DMSO-d$_6$) δ ppm 7.41 (dd, J = 8.5, 2.0 Hz, 1 H), 7.55 (d, J = 2.0 Hz, 1 H), 7.98 (d, J = 8.5 Hz, 1 H), 8.49 (br. s., 2 H), 10.79-13.69 (m, 1 H) | 196 |
| 7 | methyl 2-amino-4-hydroxyquinazoline-7-carboxylate | $^1$H NMR (400 MHz, DMSO-d$_6$) δ ppm 3.87-3.95 (m, 3 H), 7.12-7.47 (m, 1 H), 7.83 (dd, J = 8.3, 1.4 Hz, 1 H), 7.99 (d, J = 1.3 Hz, 1 H), 8.07-8.13 (m, 1 H), 8.43 (br. s., 2 H) | 220 |
| 8 | 5-methyl-2-amino-quinazolin-4-ol | Not available | 174 (M − H)− |

TABLE I-continued

Compounds of formula (III).
The following intermediates were prepared according to the method to prepare III-1.

| # | STRUCTURE | H NMR | LCMS (M + H)+ |
|---|---|---|---|
| 9 | (5-methoxy-4-hydroxy-2-amino quinazoline structure) | $^1$H NMR (400 MHz, DMSO-d$_6$) δ ppm 3.74-3.82 (m, 3 H), 6.42 (br. s., 2 H), 6.62 (d, J = 7.7 Hz, 1 H), 6.75 (dd, J = 8.3, 0.8 Hz, 1 H), 7.44 (t, J = 8.3 Hz, 1 H), 10.91 (br. s., 1 H) | 192 |
| 10 | (5-bromo-8-fluoro-4-hydroxy-2-amino quinazoline structure) | $^1$H NMR (400 MHz, DMSO-d$_6$) δ ppm 7.40 (dd, J = 8.7, 4.7 Hz, 1 H), 7.48 (t, J = 8.8 Hz, 1 H) | NA |

General Procedure of Making Compound IV

Compound III (1.5 mmol) and DBU (3.75 mmol) were dissolved in 5 mL DMF in a 30 mL glass vial. After 5 minutes BOP (1.5 mmol) was added. The reaction mixture was stirred for 5 minutes and then the amine (2.25 mmol) was added. The reaction mixture was stirred overnight. The crude reaction mixture was purified by prep. HPLC on (RP Vydac Denali C18-10 μm, 250 g, 5 cm). Mobile phase (0.25% NH$_4$HCO$_3$ solution in water, MeOH), the desired fractions were collected, evaporated, dissolved in MeOH and evaporated again to obtain the product as a solid.

General Procedure to Make Compounds 22, 23, 24, 26, 27 and 28

Compound 8 of formula (I) (see table II) (2.1 g, 6.5 mmol) was dispensed in THF (50 mL), LiOH (409 mg, 9.74 mmol) was added followed by MeOH (5 mL). The reaction mixture was stirred overnight at room temperature. The solvents were evaporated until only water remained. 10 mL 1M HCl was added and the compound was extracted with 2-methyltetrahydrofuran (2×25 mL). The combined organic layers were dried on MgSO$_4$ and the solvents were removed under reduced pressure to obtain 2-amino-4-[1-(2-pyridyl)ethylamino]quinazoline-7-carboxylic acid as a white solid.

2-amino-4-[1-(2-pyridyl)ethylamino]quinazoline-7-carboxylic acid (200 mg, 0.65 mmol) and PyBOP (421 mg, 0.81 mmol) were dissolved in DMF (5 mL) in a 30 mL glass vial. After 5 minutes Hunig's base (0.557 mL, 3.23 mmol) was added. The reaction mixture was stirred for 5 minutes and then the amine was added. The reaction mixture was stirred overnight. The crude reaction mixture was purified by preparative. HPLC on (RP Vydac Denali C18-10 μm, 250 g, 5 cm). Mobile phase (0.25% NH$_4$HCO$_3$ solution in water, MeOH), the desired fractions were collected, evaporated, dissolved in MeOH and evaporated again to obtain the product as a solid.

Procedure to Make Compound 29

Compound 12 of formula (I) (see table II) (1500 mg, 4.78 mmol) and pyridine hydrochloride (3.32 g, 28.7 mmol) were dissolved in pyridine (20 mL) and heated to 120° C. for 16 h. Pyridine was removed under reduced pressure. The residual fraction was quenched with a NaHCO$_3$ (sat.,aq.) solution. The precipitate was filtered off, washed with water and dried under vacuum at 50° C. to afford a brown solid which was purified by preparative HPLC (Stationary phase: RP Vydac Denali C18-10 μm, 200 g, 5 cm), Mobile phase: 0.25% NH$_4$HCO$_3$ solution in water, CH$_3$CN), the desired fractions were collected, evaporated, dissolved in MeOH and evaporated again to obtain 2-amino-4-[(5-methylisoxazol-3-yl)methylamino]quinazolin-5-ol (100 mg) as a solid.

2-amino-4-[(5-methylisoxazol-3-yl)methylamino]quinazolin-5-ol (40 mg, 0.15 mmol) and Cs$_2$CO$_3$ (144 mg, 0.44 mmol) were dissolved in DMF (7.5 mL) and stirred at room temperature for 30 minutes. 2-bromoethyl methyl ether (0.018 mL, 0.18 mmol) was added and the entire mixture was stirred for 16 hours at room temperature. The solvent was removed under reduced pressure and the crude residue was neutralized with 1M HCl and purified by preparative HPLC on (RP Vydac Denali C18-10 μm, 250 g, 5 cm). Mobile phase (0.25% NH$_4$HCO$_3$ solution in water, MeOH), the desired fractions were collected, evaporated, dissolved in MeOH and evaporated again to obtain compound 29 as a solid.

Procedure to Make Compound 30

A 75-mL stainless steel autoclave was charged under N$_2$ atmosphere with 2-amino-5-bromo-quinazolin-4-ol (3 g, 12.5 mmol), Pd(OAc)$_2$ (56 mg, 0.25 mmol), 1,3 bis(diphenylphosphino)propane (206 mg, 0.5 mmol), potassium acetate (2.45 g, 25 mmol), methanol (25 mL) and THF (30 mL). The autoclave was closed and pressurized to 50 bar CO gas and the reaction was carried out for 16 hours at 100° C. The formed precipitate was removed by filtration yielding methyl 2-amino-4-hydroxy-quinazoline-5-carboxylate (2.35 g).

Methyl 2-amino-4-hydroxy-quinazoline-5-carboxylate (2.35 g) in THF (10 mL) was cooled to 0° C. Then LiAlH$_4$ was added. The mixture was allowed to reach room temperature and stirred for 16 hours. EtOAc (5 mL) was added drop wise at 0° C., then 3 g Na$_2$SO$_4$.10H$_2$O was added and the entire mixture was stirred for 30 minutes. The precipitate was filtered off, and the filtrate was dried with MgSO$_4$, filtered and evaporated to dryness to obtain 2-amino-5-(hydroxymethyl)quinazolin-4-ol (750 mg) as a yellow solid.

2-amino-5-(hydroxymethyl)quinazolin-4-ol (300 mg, 1.57 mmol) was suspended in THF (20 mL) with DBU (0.586 mL, 3.92 mmol), after 5 minutes BOP (833 mg, 1.88 mmol) was added. After 15 minutes (5-methyl-3-isoxazolyl)

methylamine (0.320 mL, 3.14 mmol) was added. The mixture was stirred for 16 hours at room temperature. The solvent was removed under reduced pressure and the crude product was purified by preparative HPLC on (RP Vydac Denali C18-10 μm, 250 g, 5 cm). Mobile phase (0.25% NH$_4$HCO$_3$ solution in water, MeOH), the desired fractions were collected, evaporated, dissolved in MeOH and evaporated again to obtain compound 30 as a solid (119 mg).

Procedure to Make Compound 31

A freshly prepared NaOMe solution (1.25 mL, 6.25 mmol) was added under N$_2$ atmosphere to a mixture of 2-amino-5-bromo-8-fluoro-quinazolin-4-ol (500 mg, 1.94 mmol), copper (I) bromide (39 mg, 0.27 mmol), EtOAc (0.076 mL, 0.78 mmol) in MeOH (5 mL). The mixture was heated up in a pressure vessel to reflux for 16 hours. The solvent was removed under reduced pressure. The residue was purified by preparative HPLC (Stationary phase: RP Vydac Denali C18-10 μm, 200 g, 5 cm), Mobile phase: 0.25% NH$_4$HCO$_3$ solution in water, MeOH), the desired fractions were collected, evaporated, dissolved in MeOH and evaporated again to obtain 2-amino-8-fluoro-5-methoxy-quinazolin-4-ol (150 mg) as a solid.

2-amino-8-fluoro-5-methoxy-quinazolin-4-ol (150 mg, 0.72 mmol) was dispensed in DMF (10 mL), DBU (0.536 mL, 3.59 mmol), was added and then BOP reagent (396 mg, 0.90 mmol) was added. The reaction mixture was stirred and when it was homogeneous (5-methyl-3-isoxazolyl)methylamine (0.115 mL, 1.08 mmol) was added. The reaction mixture was stirred 16 hours. The reaction was concentrated under reduced pressure and the residue was purified by preparative HPLC (Stationary phase: RP Vydac Denali C18-10 μm, 200 g, 5 cm), Mobile phase: 0.25% NH$_4$HCO$_3$ solution in water, MeOH), the desired fractions were collected, evaporated, dissolved in MeOH and evaporated again to obtain compound 31 as a solid (64 mg).

Procedure to Make Compound 32

Compound 31 (52.5 mg, 0.173 mmol) and pyridine hydrochloride (0.12 g, 1.039 mmol) in 1 mL pyridine was heated to 120° C. for 16 hours. The volatiles were removed under reduced pressure. The residue was quenched with a NaHCO$_3$ (sat., aq.) solution. The precipitate was filtered off, washed with water and dried under vacuum at 50° C. to afford 2-amino-8-fluoro-4-[(5-methylisoxazol-3-yl)methylamino]quinazolin-5-ol (10 mg) as a brown solid. 2-amino-8-fluoro-4-[(5-methylisoxazol-3-yl)methylamino]quinazolin-5-ol (10 mg, 0.035 mmol) and Cs$_2$CO$_3$ (33.8 mg, 0.104 mmol) in DMF (5 mL) was stirred at room temperature for 30 minutes. 2-chloroethyl methyl ether (4.1 mg, 0.043 mmol) was added and the entire mixture was stirred for 16 hours at room temperature. The solvent was removed under reduced pressure. The residue was dissolved in MeOH and the precipitate (salts) were removed by filtration. The filtrate was concentrated under reduced pressure and the crude residue was purified by preparative HPLC on (Stationary phase: RP SunFire Prep C18 OBD-10 μm, 30×150 mm), Mobile phase: 0.25% NH$_4$HCO$_3$ solution in water, CH$_3$CN), the desired fractions were collected, evaporated, dissolved in MeOH and evaporated again to obtain compound 32 as a solid (2 mg).

TABLE II

Compounds of formula (I).
The following compounds were synthesized according to one of the methods described above.

| # | STRUCTURE | H NMR |
|---|---|---|
| 1 | 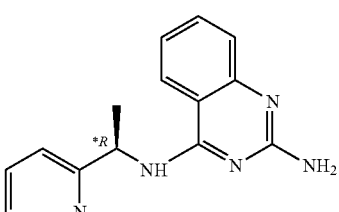 | $^1$H NMR (400 MHz, DMSO-d$_6$) δ ppm 1.60 (d, J = 7.3 Hz, 3 H), 5.61 (quin, J = 7.3 Hz, 1 H), 5.97 (s, 2 H), 7.05 (ddd, J = 8.1, 6.9, 1.2 Hz, 1 H), 7.20 (dd, J = 8.4, 0.7 Hz, 1 H), 7.24 (ddd, J = 7.5, 4.8, 0.9 Hz, 1 H), 7.44 (d, J = 7.9 Hz, 1 H), 7.49 (ddd, J = 8.3, 6.9, 1.3 Hz, 1 H), 7.72 (td, J = 7.7, 1.8 Hz, 1 H), 8.05 (d, J = 7.9 Hz, 1 H), 8.18 (dd, J = 8.3, 1.0 Hz, 1 H), 8.50-8.56 (m, 1 H) |
| 2 | 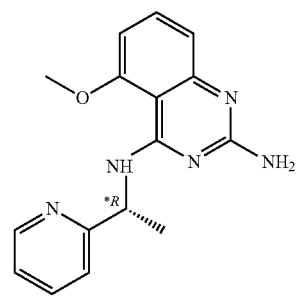 [SMILES: COc1cccc2nc(N)nc(N[C@H](C)c3ccccn3)c12] | $^1$H NMR (400 MHz, DMSO-d$_6$) δ ppm 1.53 (d, J = 6.82 Hz, 3 H) 3.99 (s, 3 H) 5.43 (t, J = 6.82 Hz, 1 H) 6.03 (s, 2 H) 6.53-6.69 (m, 1 H) 6.81 (dd, J = 8.36, 0.88 Hz, 1 H) 7.32 (ddd, J = 7.48, 4.84, 1.10 Hz, 1 H) 7.38 (t, J = 8.14 Hz, 1 H) 7.46 (d, J = 7.92 Hz, 1 H) 7.80 (td, J = 7.70, 1.76 Hz, 1 H) 8.54-8.72 (m, 1 H) 9.01 (d, J = 7.04 Hz, 1 H) |

TABLE II-continued

Compounds of formula (I).
The following compounds were synthesized according to one of the methods described above.

| # | STRUCTURE | H NMR |
|---|---|---|
| 3 | 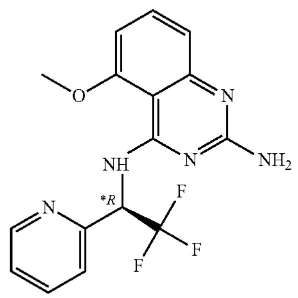 [SMILES: COc1cccc2nc(N)nc(N[C@H](c3ccccn3)C(F)(F)F)c12] | $^1$H NMR (400 MHz, DMSO-d$_6$) δ ppm 4.05 (s, 3 H), 6.25 (s, 2 H), 6.43 (quin, J = 7.8 Hz, 1 H), 6.62-6.68 (m, 1 H), 6.86 (dd, J = 8.4, 0.9 Hz, 1 H), 7.44 (t, J = 8.1 Hz, 1 H), 7.52 (ddd, J = 7.7, 4.8, 1.1 Hz, 1 H), 7.69 (d, J = 7.7 Hz, 1 H), 7.95 (td, J = 7.7, 1.8 Hz, 1 H), 8.74-8.79 (m, 1 H), 9.31 (d, J = 8.4 Hz, 1 H) |
| 4 | 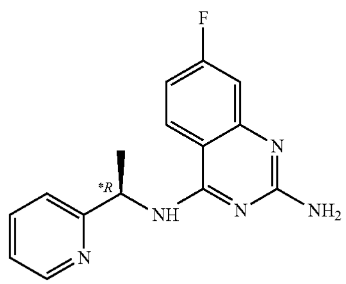 [SMILES: C[C@@H](Nc1nc(N)nc2cc(F)ccc12)c1ccccn1] | $^1$H NMR (400 MHz, CHLOROFORM-d) δ ppm 1.60 (d, J = 6.6 Hz, 3 H), 5.34 (br. s., 2 H), 5.49 (t, J = 6.8 Hz, 1 H), 6.78 (td, J = 8.6, 2.6 Hz, 1 H), 7.02 (dd, J = 10.8, 2.6 Hz, 1 H), 7.19 (ddd, J = 7.5, 4.8, 1.1 Hz, 1 H), 7.26-7.31 (m, 1 H), 7.59 (d, J = 6.8 Hz, 1 H), 7.65 (td, J = 7.6, 1.9 Hz, 1 H), 7.73 (dd, J = 9.0, 5.9 Hz, 1 H), 8.53-8.61 (m, 1 H) |
| 5 | 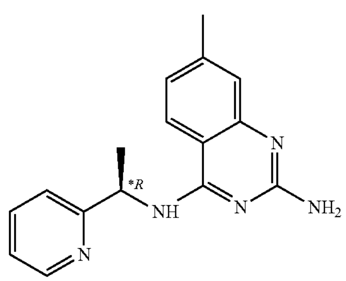 [SMILES: Cc1ccc2c(N[C@H](C)c3ccccn3)nc(N)nc2c1] | $^1$H NMR (400 MHz, DMSO-d$_6$) δ ppm 1.58 (d, J = 7.0 Hz, 3 H), 2.35 (s, 3 H), 5.59 (quin, J = 7.3 Hz, 1 H), 5.94 (s, 2 H), 6.90 (dd, J = 8.3, 1.2 Hz, 1 H), 7.01 (s, 16 H), 7.23 (dd, J = 6.9, 5.2 Hz, 1 H), 7.43 (d, J = 7.9 Hz, 1 H), 7.72 (td, J = 7.7, 1.8 Hz, 1 H), 7.97 (d, J = 7.9 Hz, 1 H), 8.07 (d, J = 8.4 Hz, 1 H), 8.48-8.57 (m, 1 H) |
| 6 | 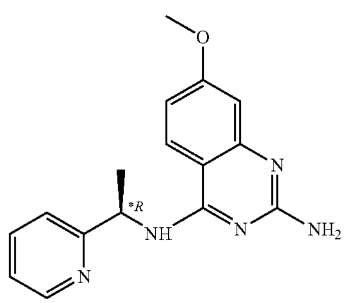 [SMILES: COc1ccc2c(N[C@H](C)c3ccccn3)nc(N)nc2c1] | $^1$H NMR (400 MHz, DMSO-d$_6$) δ ppm 1.57 (d, J = 7.04 Hz, 3 H) 3.80 (s, 3 H) 5.58 (t, J = 7.37 Hz, 1 H) 5.89 (s, 2 H) 6.61 (d, J = 2.42 Hz, 1 H) 6.67 (dd, J = 8.91, 2.53 Hz, 1 H) 7.23 (ddd, J = 7.48, 4.84, 0.88 Hz, 1 H) 7.42 (d, J = 7.92 Hz, 1 H) 7.72 (td, J = 7.70, 1.76 Hz, 1 H) 7.89 (d, J = 8.14 Hz, 1 H) 8.08 (d, J = 9.02 Hz, 1 H) 8.52 (dt, J = 3.96, 0.88 Hz, 1 H) |
| 7 | 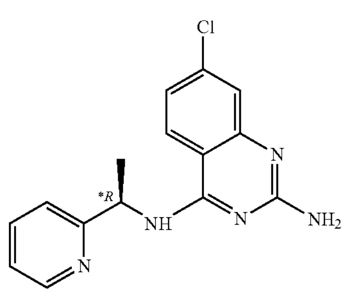 [SMILES: C[C@@H](Nc1nc(N)nc2cc(Cl)ccc12)c1ccccn1] | $^1$H NMR (400 MHz, DMSO-d$_6$) δ ppm 1.59 (d, J = 7.3 Hz, 3 H), 5.53-5.65 (m, 1 H), 6.21 (br. s., 2 H), 7.07 (dd, J = 8.7, 2.1 Hz, 1 H), 7.18 (d, J = 2.0 Hz, 1 H), 7.24 (ddd, J = 7.4, 4.8, 1.0 Hz, 1 H), 7.43 (d, J = 7.9 Hz, 1 H), 7.73 (td, J = 7.6, 1.9 Hz, 1 H), 8.19 (d, J = 7.9 Hz, 1 H), 8.23 (d, J = 8.8 Hz, 1 H), 8.50-8.56 (m, 1 H) |

TABLE II-continued

Compounds of formula (I).
The following compounds were synthesized according to one of the methods described above.

| # | STRUCTURE | H NMR |
|---|---|---|
| 8 | 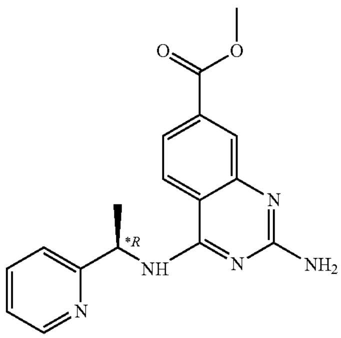 [SMILES: COC(=O)c1ccc2c(N[C@H](C)c3ccccn3)nc(N)nc2c1] | ¹H NMR (400 MHz, DMSO-$d_6$) δ ppm 1.60 (d, J = 7.0 Hz, 3 H), 3.88 (s, 3 H), 5.61 (quin, J = 7.2 Hz, 1 H), 6.22 (s, 2 H), 7.25 (ddd, J = 7.5, 4.8, 0.9 Hz, 1 H), 7.45 (d, J = 7.9 Hz, 1 H), 7.54 (dd, J = 8.6, 1.8 Hz, 1 H), 7.70-7.77 (m, 2 H), 8.28 (d, J = 7.9 Hz, 1 H), 8.32 (d, J = 8.6 Hz, 1 H), 8.51-8.57 (m, 1 H) |
| 9 | 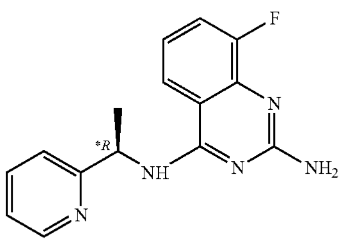 [SMILES: C[C@@H](Nc1nc(N)nc2c(F)cccc12)c1ccccn1] | ¹H NMR (400 MHz, DMSO-$d_6$) δ ppm 1.60 (d, J = 7.04 Hz, 3 H) 5.61 (quin, J = 7.26 Hz, 1 H) 6.25 (br. s., 2 H) 6.99 (td, J = 7.98, 4.95 Hz, 1 H) 7.25 (ddd, J = 7.48, 4.84, 0.88 Hz, 1 H) 7.29-7.36 (m, 1 H) 7.44 (d, J = 7.92 Hz, 1 H) 7.73 (td, J = 7.65, 1.87 Hz, 1 H) 8.01 (d, J = 8.14 Hz, 1 H) 8.17 (d, J = 8.14 Hz, 1 H) 8.52-8.59 (m, 1 H) |
| 10 | 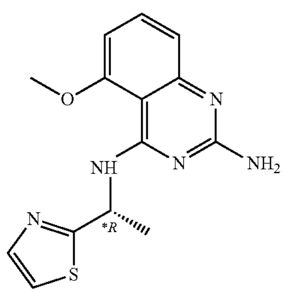 [SMILES: COc1cccc2nc(N)nc(N[C@H](C)c3nccs3)c12] | ¹H NMR (400 MHz, DMSO-$d_6$) δ ppm 1.69 (d, J = 7.0 Hz, 3 H), 3.96 (s, 3 H), 5.80 (quin, J = 7.1 Hz, 1 H), 6.09 (s, 2 H), 6.60 (dd, J = 8.0, 0.8 Hz, 1 H), 6.83 (dd, J = 8.4, 0.9 Hz, 1 H), 7.40 (t, J = 8.3 Hz, 1 H), 7.61 (d, J = 3.1 Hz, 1 H), 7.77 (d, J = 3.3 Hz, 1 H), 8.37 (d, J = 7.7 Hz, 1 H) |
| 11 | 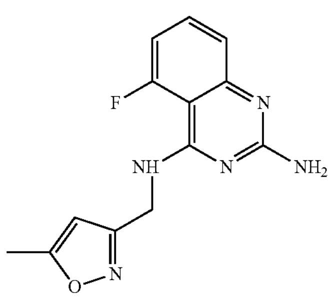 [SMILES: Cc1cc(CNc2nc(N)nc3cccc(F)c23)no1] | ¹H NMR (400 MHz, DMSO-$d_6$) δ ppm 2.35 (d, J = 0.9 Hz, 3 H), 4.72 (d, J = 5.3 Hz, 2 H), 6.22 (d, J = 0.7 Hz, 1 H), 6.35 (s, 2 H), 6.80 (ddd, J = 12.3, 7.9, 0.9 Hz, 1H), 7.04 (dd, J = 8.4, 0.9 Hz, 1 H), 7.46 (td, J = 8.2, 6.5 Hz, 1 H), 7.71-7.82 (m, 1 H) |
| 12 | 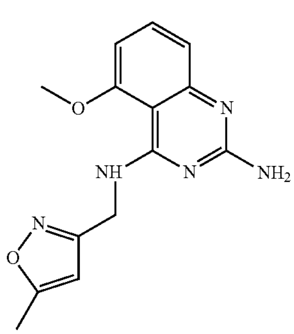 [SMILES: COc1cccc2nc(N)nc(NCc3cc(C)on3)c12] | ¹H NMR (400 MHz, DMSO-$d_6$) δ ppm 2.36 (d, J = 0.7 Hz, 3 H), 3.92 (s, 3 H), 4.70 (d, J = 5.7 Hz, 2 H), 6.05 (s, 2 H), 6.20 (d, J = 0.7 Hz, 1 H), 6.56 (dd, J = 8.0, 0.8 Hz, 1 H), 6.81 (dd, J = 8.4, 0.9 Hz, 1 H), 7.38 (t, J = 8.1 Hz, 1 H), 8.40 (t, J = 5.8 Hz, 1 H) |

TABLE II-continued

Compounds of formula (I).
The following compounds were synthesized according to one of the methods described above.

| # | STRUCTURE | H NMR |
|---|---|---|
| 13 | 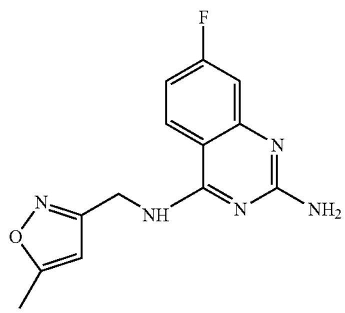 [SMILES: Cc1cc(CNc2nc(N)nc3cc(F)ccc23)no1] | $^1$H NMR (400 MHz, DMSO-d$_6$) δ ppm 2.33-2.38 (m, 3 H), 4.67 (d, J = 5.9 Hz, 2 H), 6.18-6.24 (m, 1 H), 6.27 (s, 2 H), 6.85-6.92 (m, 2 H), 7.99-8.07 (m, 1 H), 8.42 (t, J = 5.7 Hz, 1 H) |
| 14 | 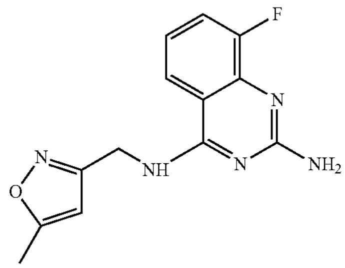 [SMILES: Cc1cc(CNc2nc(N)nc3c(F)cccc23)no1] | $^1$H NMR (400 MHz, DMSO-d$_6$) δ ppm 2.35 (d, J = 0.9 Hz, 3 H), 4.69 (d, J = 5.9 Hz, 2 H), 6.22 (d, J = 0.9 Hz, 1 H), 6.39 (br. s., 2 H), 6.98 (td, J = 8.0, 4.8 Hz, 1 H), 7.33 (ddd, J = 11.4, 7.8, 1.1 Hz, 1 H), 7.79 (d, J = 8.4 Hz, 1 H), 8.48 (t, J = 5.8 Hz, 1 H) |
| 15 | 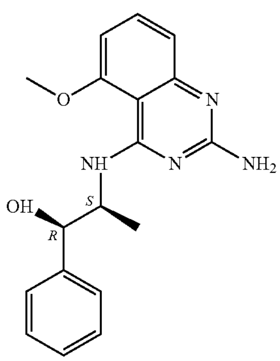 | $^1$H NMR (400 MHz, DMSO-d$_6$) δ ppm 0.97 (d, J = 6.6 Hz, 3 H), 3.92 (s, 3 H), 4.44-4.55 (m, 1 H), 4.89 (d, J = 3.1 Hz, 1 H), 5.69 (br. s., 1 H), 6.06 (s, 2 H), 6.52-6.58 (m, 1 H), 6.79 (dd, J = 8.3, 0.8 Hz, 1 H), 7.22-7.29 (m, 1 H), 7.32-7.41 (m, 3 H), 7.43-7.49 (m, 2 H), 8.07 (d, J = 7.9 Hz, 1 H) |
| 16 | 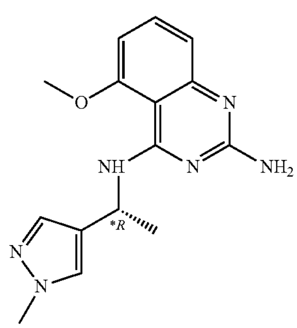 [SMILES: COc1cccc2nc(N)nc(N[C@H](C)c3cnn(C)c3)c12] | $^1$H NMR (400 MHz, DMSO-d$_6$) δ ppm 1.51 (d, J = 6.8 Hz, 3 H), 3.79 (s, 3 H), 3.90 (s, 3 H), 5.39 (quin, J = 7.0 Hz, 1 H), 6.05 (s, 2 H), 6.52-6.58 (m, 1 H), 6.79 (dd, J = 8.4, 0.9 Hz, 1 H), 7.35 (t, J = 8.3 Hz, 1 H), 7.45 (s, 1 H), 7.68 (s, 1 H), 7.84 (d, J = 7.7 Hz, 1 H) |
| 17 | 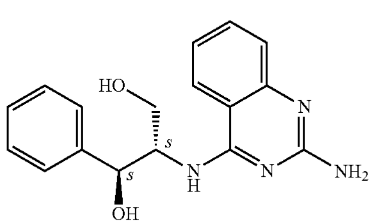 [SMILES: Nc1nc(N[C@@H](CO)[C@@H](O)c2ccccc2)c2ccccc2n1] | $^1$H NMR (400 MHz, DMSO-d$_6$) δ ppm 3.40-3.49 (m, 1 H), 3.60-3.71 (m, 1 H), 4.45-4.55 (m, 1 H), 4.79 (br. s., 1 H), 4.97-5.05 (m, 1 H), 5.62 (d, J = 4.8 6 Hz, 1 H), 5.98 (s, 2 H), 7.02 (t, J = 7.5 Hz, 1 H), 7.08 (d, J = 8.3 Hz, 1 H), 7.13-7.21 (m, 2 H), 7.27 (t, J = 7.5 Hz, 2 H), 7.38 (d, J = 7.3 Hz, 2 H), 7.42-7.50 (m, 1 H), 7.95 (d, J = 8.3 Hz, 1 H) |

TABLE II-continued

Compounds of formula (I).
The following compounds were synthesized according to one of the methods described above.

| # | STRUCTURE | H NMR |
|---|---|---|
| 18 | 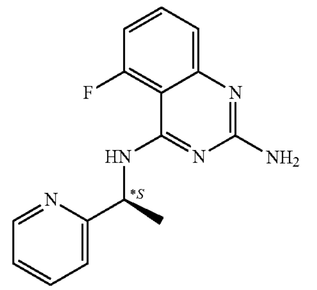 [SMILES: C[C@H](Nc1nc(N)nc2cccc(F)c12)c1ccccn1] | $^1$H NMR (400 MHz, DMSO-d$_6$) δ ppm 1.55 (d, J = 6.82 Hz, 3 H) 5.49 (td, J = 6.77, 2.09 Hz, 1 H) 6.32 (s, 2 H) 6.82 (ddd, J = 12.76. 7.92, 0.88 Hz, 1 H) 7.05 (dd, J = 8.47, 0.99 Hz, 1 H) 7.33 (ddd, J = 7.54, 4.90. 0.99 Hz, 1 H) 7.42-7.57 (m, 2 H) 7.82 (td, J = 7.70, 1.76 Hz, 1 H) 7.93 (dd, J = 14.63, 6.93 Hz, 1 H) 8.58-8.67 (m, 1 H) |
| 19 | 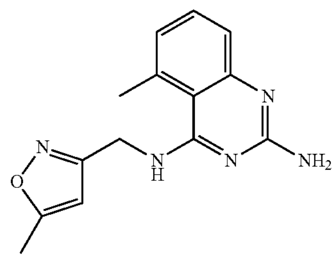 [SMILES: Cc1cc(CNc2nc(N)nc3cccc(C)c23)no1] | $^1$H NMR (400 MHz, DMSO-d$_6$) δ ppm 2.33-2.39 (m, 3 H), 2.75 (s, 3 H), 4.71 (d, J = 5.3 Hz, 2 H), 6.06 (s, 2 H), 6.22-6.26 (m, 1 H), 6.82 (d, J = 6.8 Hz, 1 H), 7.08 (d, J = 7.7 Hz, 1 H), 7.13 (t, J = 5.3 Hz, 1 H), 7.32 (dd, J = 8.4, 7.3 Hz, 1 H) |
| 20 | 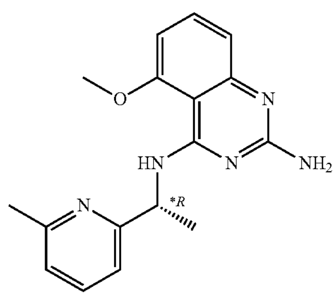 [SMILES: COc1cccc2nc(N)nc(N[C@H](C)c3cccc(C)n3)c12] | $^1$H NMR (400 MHz, DMSO-d$_6$) δ ppm 1.49 (d, J = 6.6 Hz, 3 H), 2.58 (s, 3 H), 4.02 (s, 3 H), 5.37 (quin, J = 6.6 Hz, 1 H), 6.02 (s, 2 H), 6.56-6.62 (m, 1 H), 6.816 (dd, J = 8.3. 0.8 Hz. 1 H), 7.20 (d, J = 7.5 Hz, 1 H), 7.24 (d, J = 7.7 Hz, 1 H), 7.37 (t, J = 8.1 Hz, 1 H), 7.70 (t, J = 7.7 Hz, 1 H), 9.21 (d, J = 6.8 Hz, 1 H) |
| 21 | 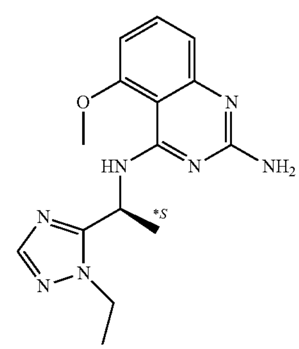 [SMILES: CCn1ncnc1[C@H](C)Nc1nc(N)nc2cccc(OC)c12] | $^1$H NMR (400 MHz, DMSO-d$_6$) δ ppm 1.36 (t, J = 7.3 Hz, 3 H), 1.57 (d, J = 6.8 Hz, 3 H), 3.95 (s, 3 H), 4.21-4.42 (m, 2 H), 5.65 (quin, J = 7.0 Hz, 1 H), 6.08 (br. s., 2 H), 6.58 (dd, J = 7.9, 0.7 Hz, 1 H), 6.81 (dd, J = 8.4, 0.7 Hz, 1 H), 7.39 (t, J = 8.1 Hz, 1 H), 7.88 (s, 1 H), 8.26 (d, J = 7.7 Hz, 1 H) |
| 22 | 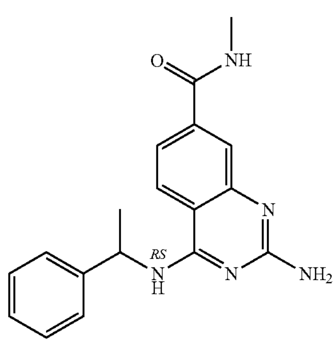 [SMILES: CNC(=O)c1ccc2c(NC(C)c3ccccc3)nc(N)nc2c1] | $^1$H NMR (400 MHz, DMSO-d$_6$) δ ppm 1.60 (d, J = 7.3 Hz, 3 H), 2.80 (d, J = 4.4 Hz, 3 H), 5.60 (quin, J = 7.3 Hz, 1 H), 6.11 (s, 2 H), 7.24 (ddd, J = 7.4, 4.8, 1.0 Hz, 1 H), 7.45 (dt, J = 8.4, 1.8 Hz, 2 H), 7.65 (d, J = 1.8 Hz, 1 H), 7.73 (td, J = 7.7, 1.8 Hz, 1 H), 8.16 (d, J = 7.9 Hz, 1 H), 8.25 (d, J = 8.4 Hz, 1 H), 8.49-8.56 (m, 2 H) |

TABLE II-continued

Compounds of formula (I).
The following compounds were synthesized according to one of the methods described above.

| # | STRUCTURE | H NMR |
|---|---|---|
| 23 | 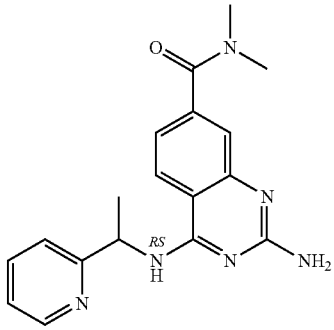 [SMILES: CC(Nc1nc(N)nc2cc(C(=O)N(C)C)ccc12)c1ccccn1] | ¹H NMR (400 MHz, DMSO-d₆) δ ppm 1.60 (d, J = 7.0 Hz, 3 H), 2.91 (s, 3 H), 3.00 (s, 3 H), 5.61 (quin, J = 7.3 Hz, 1 H), 6.12 (s, 2 H), 7.02 (dd, J = 8.3, 1.7 Hz, 16 H), 7.12 (d, J = 1.5 Hz, 1 H), 7.24 (ddd, J = 7.5, 4.8, 0.9 Hz, 1 H), 7.44 (d, J = 7.9 Hz, 1 H), 7.73 (td, J = 7.7, 1.8 Hz, 1 H), 8.16 (d, J = 7.9 Hz, 1 H), 8.24 (d, J = 8.4 Hz, 1 H), 8.51-8.56 (m, 1 H) |
| 24 | 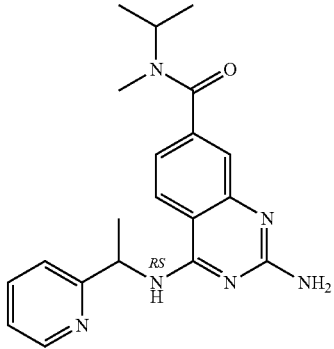 [SMILES: CC(Nc1nc(N)nc2cc(C(=O)N(C)C(C)C)ccc12)c1ccccn1] | ¹H NMR (400 MHz, DMSO-d₆) δ ppm 1.03-1.20 (m, 6 H), 1.60 (d, J = 7.0 Hz, 3 H), 2.68-2.89 (m, 3 H), 3.76-3.91 (m, 1 H), 5.61 (quin, J = 7.2 Hz, 1 H), 6.13 (br. s., 2 H), 6.94-7.02 (m, 1 H), 7.02-7.12 (m, 1 H), 7.24 (ddd, J = 7.4, 4.8, 1.0 Hz, 1 H), 7.44 (s, 1 H), 7.73 (td, J = 7.7, 2.0 Hz. 1 H), 8.15 (s, 1 H), 8.23 (s, 1 H), 8.50-8.57 (m, 1 H) |
| 25 | 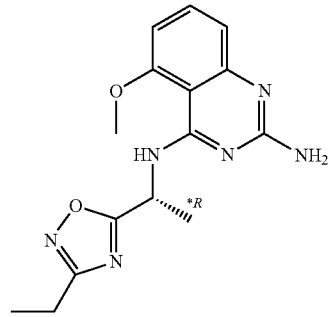 [SMILES: CCc1noc([C@@H](C)Nc2nc(N)nc3cccc(OC)c23)n1] | ¹H NMR (400 MHz, DMSO-d₆) δ ppm 1.23 (t, J = 7.5 Hz, 3 H), 1.68 (d, J = 7.0 Hz, 3 H), 2.71 (q, J = 7.6 Hz, 2 H), 3.96 (s, 3 H), 5.71 (quin, J = 7.2 Hz, 1 H), 6.05 (br. s., 2 H), 6.57-6.62 (m, 1 H), 6.83 (dd, J = 8.5, 0.8 Hz, 1 H), 7.41 (t, J = 8.1 Hz, 1 H), 8.31 (d, J = 7.5 Hz, 1 H) |
| 26 | 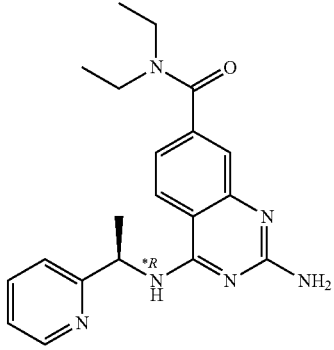 [SMILES: CCN(CC)C(=O)c1ccc2c(N[C@H](C)c3ccccn3)nc(N)nc2c1] | ¹H NMR (400 MHz, DMSO-d₆) δ ppm 1.05 (br. s., 3 H), 1.16 (br. s., 3 H), 1.60 (d, J = 7.0 Hz, 3 H), 3.20 (br. s., 2 H), 3.43 (br. s., 2 H), 5.60 (quin, J = 7.3 Hz, 1 H), 6.11 (s, 2 H), 6.97 (dd, J = 8.3, 1.7 Hz, 1 H), 7.05 (d, J = 1.3 Hz, 1 H), 7.24 (ddd, J = 7.4, 4.8, 1.0 Hz, 1 H), 7.45 (d, J = 7.9 Hz, 1 H), 7.73 (td, J = 7.6, 1.9 Hz, 1 H), 8.15 (d, J = 7.9 Hz, 1 H), 8.24 (d, J = 8.4 Hz, 1 H), 8.50-8.56 (m, 1 H) |

TABLE II-continued

Compounds of formula (I).
The following compounds were synthesized according to one of the methods described above.

| # | STRUCTURE | H NMR |
|---|---|---|
| 27 | 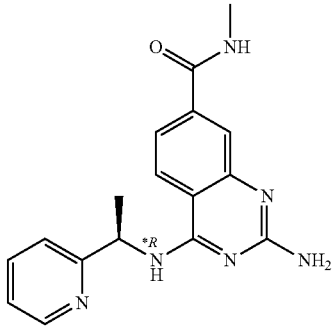 [SMILES: CNC(=O)c1ccc2c(N[C@H](C)c3ccccn3)nc(N)nc2c1] | $^1$H NMR (400 MHz, DMSO-$d_6$) δ ppm 1.60 (d, J = 7.0 Hz, 3 H), 2.79 (d, J = 4.4 Hz, 3 H), 5.60 (quin, J = 7.3 Hz, 1 H), 6.09 (s, 2 H), 7.24 (ddd, J = 7.4, 4.8, 1.0 Hz, 1 H), 7.41-7.48 (m, 2 H), 7.65 (d, J = 1.5 Hz, 1 H), 7.73 (td, J = 7.7, 2.0 Hz, 1 H), 8.15 (d, J = 7.9 Hz, 1 H), 8.24 (d, J = 8.6 Hz, 1 H), 8.48-8.56 (m, 2 H) |
| 28 | 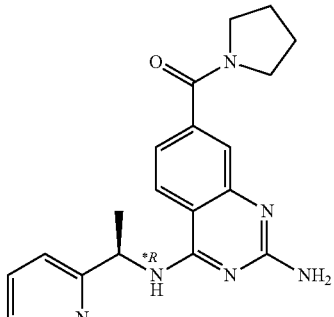 | $^1$H NMR (400 MHz, DMSO-$d_6$) δ ppm 1.60 (d, J = 7.0 Hz, 3 H), 1.76-1.93 (m, 4 H), 3.37 (t, J = 6.5 Hz, 2 H), 3.47 (t, J = 6.8 Hz, 2 H), 5.60 (quin, J = 7.2 Hz, 1 H), 6.10 (s, 2 H), 7.12 (dd, J = 8.3, 1.7 Hz, 1 H), 7.22 (d, J = 1.5 Hz, 1 H), 7.23-7.26 (m, 1 H), 7.44 (d, J = 7.9 Hz, 1 H), 7.73 (td, J = 7.7, 1.8 Hz, 1 H), 8.15 (d, J = 7.9 Hz, 1 H), 8.23 (d, J = 8.6 Hz, 1 H), 8.50-8.56 (m, 1 H) |
| 29 | 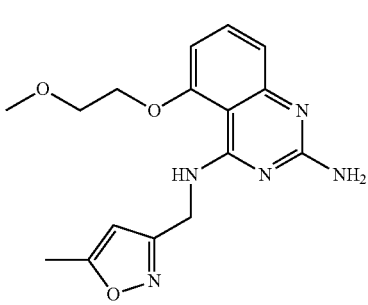 [SMILES: COCCOc1cccc2nc(N)nc(NCc3cc(C)on3)c12] | $^1$H NMR (400 MHz, DMSO-$d_6$) δ ppm 2.33-2.42 (m, 3 H) 3.27 (s, 3 H) 3.64-3.80 (m, 2 H) 4.16-4.31 (m, 2 H) 4.69 (d, J = 5.50 Hz, 2 H) 6.12 (s, 2 H) 6.21-6.29 (m, 1 H) 6.59 (d, J = 7.48 Hz, 1 H) 6.82 (d, J = 7.70 Hz, 1 H) 7.37 (t, J = 8.25 Hz, 1 H) 8.37 (s, 1 H) |
| 30 | 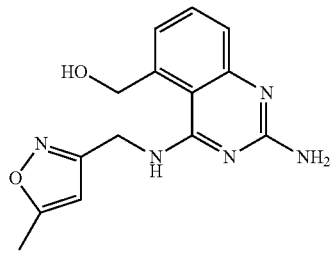 [SMILES: Cc1cc(CNc2nc(N)nc3cccc(CO)c23)no1] | $^1$H NMR (400 MHz, DMSO-$d_6$) δ ppm 0.87 (t, J = 7.26 Hz, 3 H) 1.23-1.38 (m, 2 H) 1.38-1.49 (m, 2 H) 1.54 (d, J = 7.04 Hz, 3 H) 3.33-3.50 (m, 2 H) 5.38 (t, J = 7.26 Hz, 1 H) 6.10 (s, 2H) 7.05 (dd, J = 7.04, 1.32 Hz, 1 H) 7.30 (dd, J = 8.47, 1.21 Hz, 1 H) 7.48 (dd, J = 8.36, 7.04 Hz, 1 H) 7.53 (dd, J = 1.87, 0.77 Hz, 1 H) 7.68 (t, J = 4.73 Hz, 1 H) 9.09 (d, J = 1.98 Hz, 1 H) 9.39 (d, J = 8.14 Hz, 1 H) |

TABLE II-continued

Compounds of formula (I).
The following compounds were synthesized according to one of the methods described above.

| # | STRUCTURE | H NMR |
|---|---|---|
| 31 | 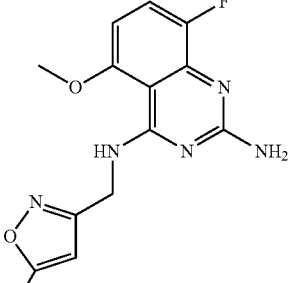 | $^1$H NMR (400 MHz, DMSO-$d_6$) δ ppm 2.28-2.40 (m, 3 H) 3.90 (s, 3 H) 4.71 (d, J = 5.94 Hz, 2 H) 6.21 (d, J = 0.88 Hz, 1 H) 6.33 (br. s., 2 H) 6.46 (dd, J = 8.80, 3.52 Hz, 1 H) 7.26 (dd, J = 10.89, 8.69 Hz, 1 H) 8.49 (t, J = 5.72 Hz, 1 H) |
| 32 | 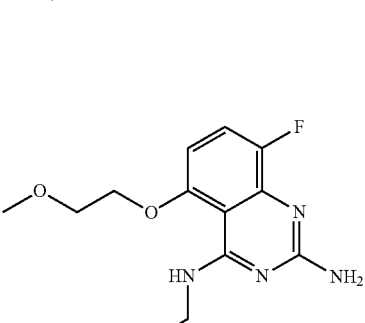 | Not available |

SFC Purification Methods.

General Procedure

The Supercritical Fluid Chromatography (SFC) separation was performed with supercritical $CO_2$ and a modifier as specified in the table using a column as specified in the table.

TABLE III

Compounds of formula (I). The following compounds were isolated SFC separation.

| # | Column | Modifier |
|---|---|---|
| 1 | Chiralpak Diacel AS 20 × 250 mm | iPrOH with 0.2% iPrNH2 |
| 2 | Chiralpak Diacel AS 20 × 250 mm | MeOH with 0.2% iPrNH2 |
| 3 | Chiralpak Diacel AS 20 × 250 mm | iPrOH with 0.2% iPrNH2 |
| 4 | Chiralpak Diacel AD 30 × 250 mm | iPrOH with 0.2% iPrNH2 |
| 5 | Chiralpak Diacel AS 20 × 250 mm | iPrOH with 0.4% iPrNH2 |
| 6 | Chiralpak Diacel AS 20 × 250 mm | EtOH with 0.2% iPrNH2 |
| 7 | Chiralpak Diacel AS 20 × 250 mm | iPrOH with 0.2% iPrNH2 |
| 8 | Chiralpak Diacel AS 20 × 250 mm | iPrOH with 0.2% iPrNH2 |
| 9 | Chiralpak Diacel AD 30 × 250 mm | EtOH with 0.2% iPrNH2 |
| 10 | Chiralpak Diacel AS 20 × 250 mm | EtOH with 0.4% iPrNH2 |
| 16 | Chiralpak Diacel AD 30 × 250 mm | EtOH with 0.2% iPrNH2 |
| 18 | Chiralpak Diacel AS 20 × 250 mm | iPrOH with 0.2% iPrNH2 |
| 20 | Chiralpak Diacel AS 20 × 250 mm | EtOH with 0.2% iPrNH2 |
| 21 | Chiralpak Diacel AD 30 × 250 mm | EtOH with 0.2% iPrNH2 |
| 25 | Chiralpak Diacel AD 30 × 250 mm | MeOH with 0.4% iPrNH2 |
| 26 | Chiralpak Diacel AD 30 × 250 mm | EtOH with 0.2% iPrNH2 |
| 27 | Chiralpak Diacel AD 30 × 250 mm | MeOH with 0.4% iPrNH2 |
| 28 | Chiralpak Diacel AD 30 × 250 mm | EtOH with 0.4% iPrNH2 |

For all compounds the first eluting compound was assigned as *R.

*R means an enantiomeric pure configuration of which the absolute stereochemistry is unknown.

Analytical Methods.

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]$^+$ (protonated molecule) and/or [M−H]$^−$ (deprotonated molecule). In case the compound was not directly ionizable the type of adduct is specified (i.e. [M+NH$_4$]$^+$, [M+HCOO]$^−$, etc. . . . ). For molecules with multiple isotopic patterns (Br, Cl.), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

TABLE IV

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| B7010 B7014 | Waters: Acquity ® UPLC ® - DAD and SQD | Waters: HSS T3 (1.8 μm, 2.1*100 mm) | A: 95% CH$_3$COONH$_4$ 10 mM + 5% CH$_3$CN B: CH$_3$CN | From 100% A to 5% A in 2.10 min, to 0% A in 0.90 min, to 5% A in 0.5 min | 0.8 55 | 3.5 |
| B8011 B8002 | Waters: Acquity ® UPLC ® - DAD and SQD | Waters: BEH C18 (1.7 μm, 2.1*50 mm) | A: 95% CH$_3$COONH$_4$ 10 mM + 5% CH$_3$CN B: CH$_3$CN | From 95% A to 5% A in 1.3 min, held for 0.7 min. | 0.8 55 | 2 |
| B9007 B9008 | Waters: Acquity ® UPLC ® - DAD and SQD | Waters: HSS T3 (1.8 μm, 2.1*100 mm) | A: 95% CH$_3$COONH$_4$ 10 mM + 5% CH$_3$CN B: CH$_3$CN | From 100% A to 5% A in 2.10 min, to 0% A in 0.90 min, to 5% A in 0.5 min | 0.8 55 | 3.5 |

TABLE V

Compounds of formula (I). The following compounds were characterized according to one of the methods described above.

| # | Method code | Retention Time (min) | Mass Found (M + H) |
|---|---|---|---|
| 1 | B7010B7014 | 0.61 | 266 |
| 2 | B7010B7014 | 1.59 | 296 |
| 3 | B9007B9008 | 1.61 | 350 |
| 4 | B8011B8002 | 0.69 | 284 |
| 5 | B7010B7014 | 1.39 | 280 |
| 6 | B7010B7014 | 1.31 | 296 |
| 7 | B8011B8002 | 0.78 | 300 |
| 8 | B9007B9008 | 1.32 | 324 |
| 9 | B9007B9008 | 1.29 | 284 |
| 10 | B9007B9008 | 1.31 | 302 |
| 11 | B8011B8002 | 0.69 | 274 |
| 12 | B7010B7014 | 1.26 | 286 |
| 13 | B8011B8002 | 0.64 | 274 |
| 14 | B7010B7014 | 1.32 | 274 |
| 15 | B8011B8002 | 0.77 | 325 |
| 16 | B8011B8002 | 0.62 | 299 |
| 17 | B8011B8002 | 0.53 | 311 |
| 18 | B8011B8002 | 0.79 | 284 |
| 19 | B8011B8002 | 0.65 | 270 |
| 20 | B8011B8002 | 0.84 | 310 |
| 21 | B8011B8002 | 0.61 | 314 |
| 22 | B8011B8002 | 0.56 | 323 |
| 23 | B8011B8002 | 0.59 | 337 |
| 24 | B8011B8002 | 0.70 | 365 |
| 25 | B8011B8002 | 0.75 | 315 |
| 26 | B8011B8002 | 0.69 | 365 |
| 27 | B8011B8002 | 0.56 | 323 |
| 28 | B8011B8002 | 0.66 | 363 |
| 29 | B8011B8002 | 0.70 | 330 |
| 30 | B9007B9008 | 1.04 | 286 |
| 31 | B9007B9008 | 1.36 | 304 |
| 32 | B9007B9008 | 1.46 | 348 |

Biological Activity of Compounds of Formula (I)
Description of Biological Assays
Assessment of TLR7 and TLR8 activity The ability of compounds to activate human TLR7 and/or TLR8 was assessed in a cellular reporter assay using HEK293 cells transiently transfected with a TLR7 or TLR8 expression vector and NFκB-luc reporter construct.

Briefly, HEK293 cells were grown in culture medium (DMEM supplemented with 10% FCS and 2 mM Glutamine). For transfection of cells in 15 cm dishes, cells were detached with Trypsin-EDTA, transfected with a mix of CMV-TLR7 or TLR8 plasmid (1700 ng), NFκB-luc plasmid (850 ng) and a transfection reagent and incubated for 48 h at 37° C. in a humidified 5% CO$_2$ atmosphere. Transfected cells were then washed in PBS, detached with Trypsin-EDTA and resuspended in medium to a density of 1.25×10$^5$ cells/mL. Forty microliters of cells were then dispensed into each well in 384-well plates, where 200 nL of compound in 100% DMSO was already present. Following 6 hours incubation at 37° C., 5% CO$_2$, the luciferase activity was determined by adding 15 μL of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 40 μL per well of cells transfected with the CMV-TLR7 construct alone (1.25× 10$^5$ cells/mL), in 384-well plates. Cell viability was measured after 6 hours incubation at 37° C., 5% CO$_2$ by adding 15 μL of ATP lite (Perkin Elmer) per well and reading on a ViewLux ultraHTS microplate imager (Perkin Elmer). Data was reported as CC$_{50}$.

In parallel, a similar dilution series of compound was used (200 nL of compound in 100% DMSO) with 40 μL per well of cells transfected with NFκB-luc reporter construct alone (1.25×10$^5$ cells/mL). Six hours after incubation at 37° C., 5% CO$_2$, the luciferase activity was determined by adding 15 μl of Steady Lite Plus substrate (Perkin Elmer) to each well and readout performed on a ViewLux ultraHTS microplate imager (Perkin Elmer). Counterscreen data is reported as LEC.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACT-GAAACT (SEQ ID NO: 1) is highly responsive to the STAT1-STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2\times10^5$ cells/well were dispensed into 384-well plates containing compounds (70 μL total volume). After overnight incubation, 10 μL of supernatant was transferred to 384-well plates containing $5\times10^3$ HEK-ISREluc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

TABLE VI

BIOLOGICAL ACTIVITY.

| # | Human TLR 7 (LEC) μM | Human TLR 8 (LEC) μM | HEK-ISRE luc (LEC) μM |
|---|---|---|---|
| 1 | 0.72 | >25 | 0.61 |
| 2 | 0.94 | >25 | 0.49 |
| 3 | 0.76 | >25 | 0.47 |
| 4 | 0.92 | 19.8 | 0.59 |
| 5 | 0.53 | 14.7 | 0.11 |
| 6 | 3.75 | >25 | 0.64 |
| 7 | 0.82 | 16.4 | 0.38 |
| 8 | 4.94 | NA | 2.11 |
| 9 | 5.21 | >25 | 1.68 |
| 10 | 0.42 | 12.3 | 0.11 |
| 11 | 0.45 | 3.09 | 0.082 |
| 12 | 0.047 | 1.94 | 0.036 |
| 13 | 0.46 | 5.22 | 0.12 |
| 14 | 0.65 | >25 | 0.13 |
| 15 | 0.61 | >25 | 0.56 |
| 16 | 2.44 | 9.14 | 0.55 |
| 17 | 0.83 | 5.51 | 0.16 |
| 18 | 8.25 | 24.3 | 7.83 |
| 19 | 0.11 | 1.74 | 0.051 |
| 20 | 1.46 | >25 | 0.62 |
| 21 | 6.1 | 8.85 | 0.54 |
| 22 | 14.7 | >25 | 2.20 |
| 23 | 6.67 | >25 | 1.62 |
| 24 | 14.3 | 11.0 | 1.75 |
| 25 | 1.95 | 6.62 | 0.49 |
| 26 | 2.14 | >25 | 7.33 |
| 27 | 8.24 | >25 | 5.04 |
| 28 | 2.24 | >25 | 1.57 |
| 29 | 0.082 | 8.15 | NA |
| 30 | 0.63 | 9.0 | 0.14 |
| 31 | 0.74 | >25 | 0.46 |
| 32 | NA | NA | NA |

NA = not available. All compounds showed no toxicity up to the highest tested concentration.
All compounds showed no activity (LEC >25 μM) in the HEK 293 NF-kB counterscreen assay described above.

The invention claimed is:
1. A compound of formula (I)

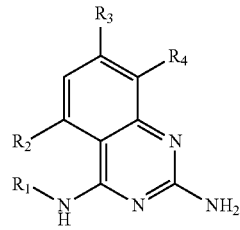

or a pharmaceutically acceptable salt, tautomer(s), stereoisomeric forms or polymorph thereof, wherein
$R_1$ is selected from the group consisting of:

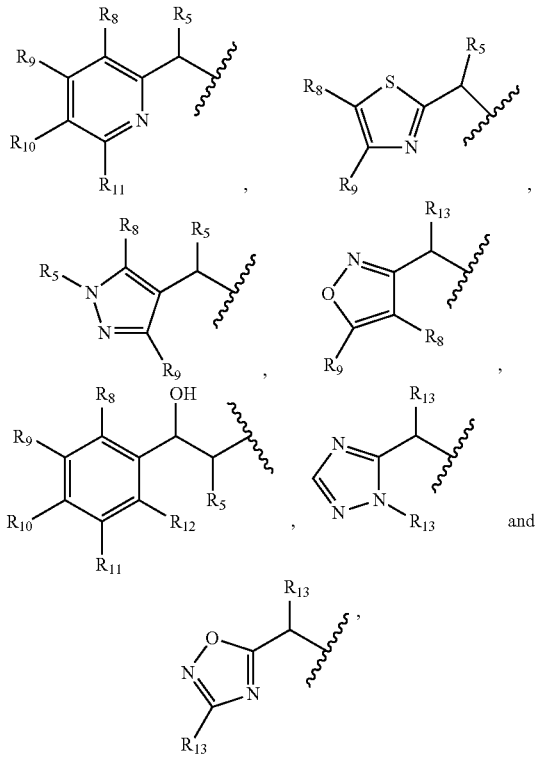

$R_2$ is selected from the group consisting of hydrogen, —O—$(C_{1-3})$-alkyl, halogen, $(C_{1-3})$-alkyl, —O—$(C_{1-3})$-alkyl-O—$(C_{1-3})$-alkyl and $CH_2OH$;
$R_3$ is selected from the group consisting of hydrogen, —O—$(C_{1-3})$-alkyl, halogen, $(C_{1-3})$-alkyl and —C(=O)—$R_7$, wherein $R_7$ is —O—$(C_{1-3})$-alkyl, $NH_2$, $NH(CH_3)$, $N(CH_3)_2$, $N(CH_3)(C_{1-3})$-alkyl, $N((C_{1-3})$-alkyl$)_2$ or pyrolidine;
$R_4$ is hydrogen or fluorine;
$R_5$ is selected from the group consisting of $(C_{1-3})$-alkyl, $(C_{1-3})$-fluoro-alkyl, and $CH_2OH$;
$R_6$ is selected from the group consisting of $NH_2$, $NH(CH_3)$, $N(CH_3)_2$, and (hetero)-aniline, wherein said (hetero)-aniline- is optionally substituted with one or more of $R_8$, $R_9$, $R_{10}$ $R_{11}$ or $R_{12}$ or (hetero)-benzylamine, wherein the (hetero)-benzylamine is optionally substituted with one or more of $R_8$, $R_9$, $R_{10}$ $R_{11}$ or $R_{12}$, wherein $R_8$, $R_9$, $R_{10}$, $R_{11}$ and $R_{12}$ which are the same or different, are each independently selected from the group consisting of hydrogen, $(C_{1-3})$-alkyl, —O—$(C_{1-3})$-alkyl and halogen; and $R_{13}$ is selected from the group consisting of hydrogen, $(C_{1-3})$-alkyl and $(C_{1-3})$-fluoro-alkyl.

2. A substituted 2-amino-4-hydroxyquinazoline having the following formula

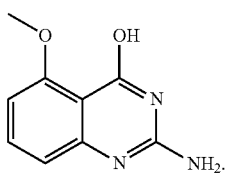
(III-1)

3. A compound of claim 1, wherein $R_1$ is

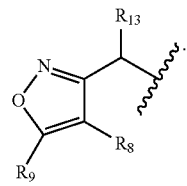

4. A compound as claimed in claim 1, wherein $R_9$ is $CH_3$.

5. A compound as claimed in claim 1, wherein $R_2$ is $OCH_3$ or —O—$(C_{1-3})$-alkyl-O—$(C_{1-3})$-alkyl.

6. A compound as claimed in claim 1, wherein $R_3$, $R_4$, $R_{13}$ and $R_8$ are each H;

$R_9$ is $CH_3$;

$R_2$ is —O—$(C_{1-3})$-alkyl-O—$(C_{1-3})$-alkyl; and $R_1$ is

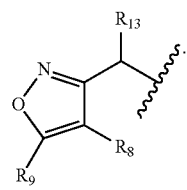

7. A compound as claimed in claim 1, wherein $R_3$, $R_4$, $R_{13}$ and $R_8$ are each H;

$R_9$ is $CH_3$;

$R_2$ is $OCH_3$; and $R_1$ is

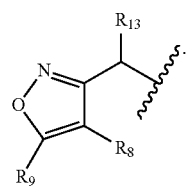

8. A compound as claimed in claim 1, said compound selected from the group consisting of

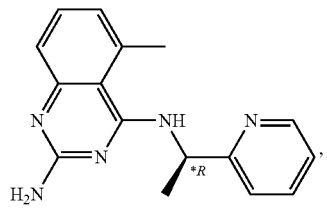

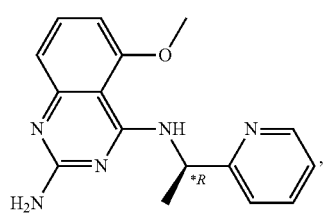

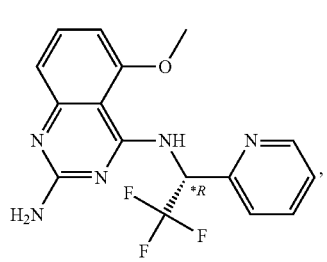

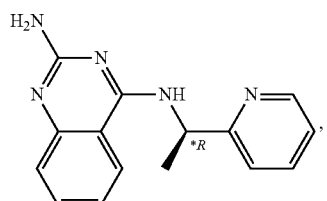

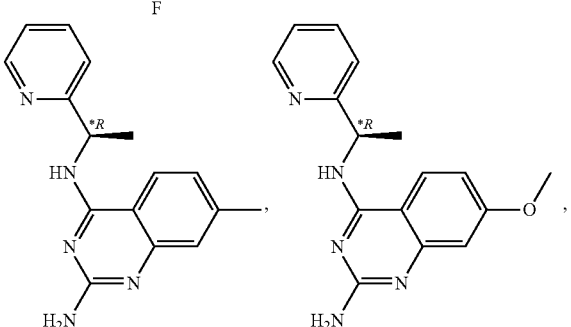

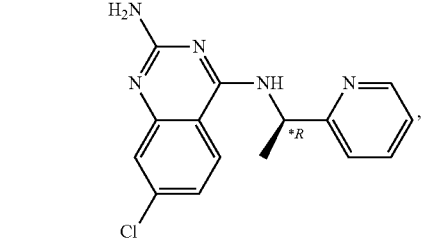

-continued

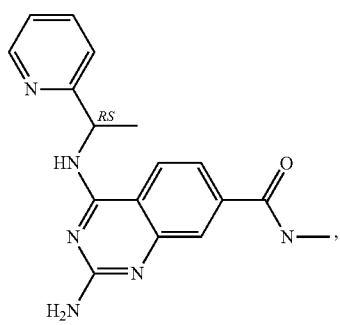
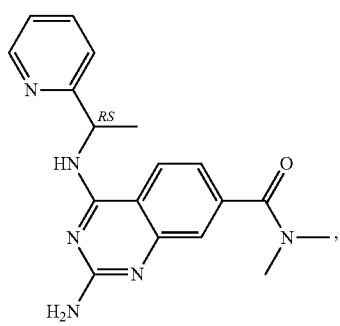
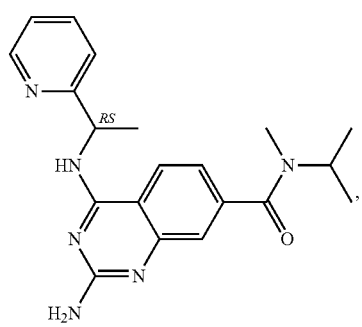
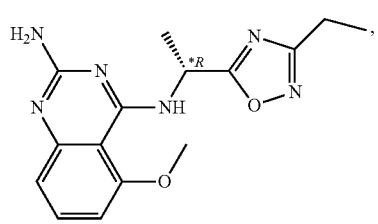
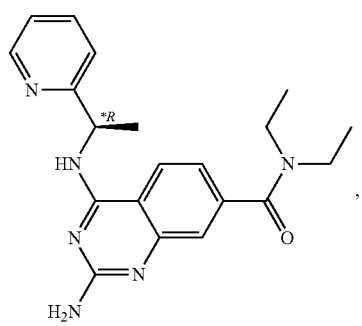
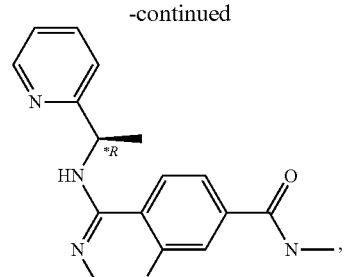
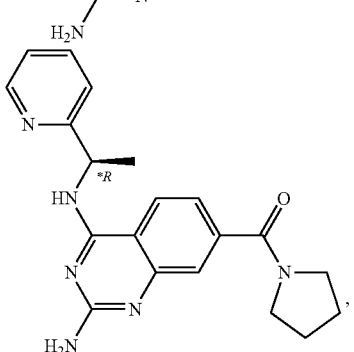
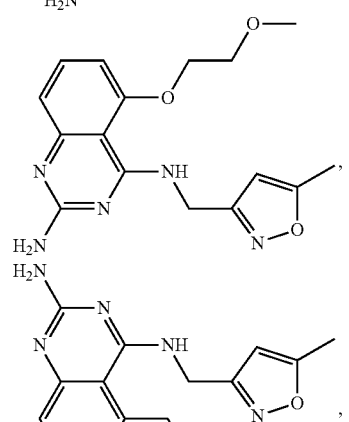
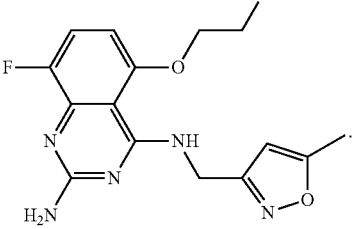
and
9. A pharmaceutical composition comprising a compound as claimed in claim 1 together with one or more pharmaceutically acceptable excipients, diluents or carriers.
* * * * *